(12) United States Patent
Flodin et al.

(10) Patent No.: US 7,572,872 B2
(45) Date of Patent: Aug. 11, 2009

(54) BIOMIMETIC MATERIALS COMPRISING POLYHEDRAL OLIGOMERIC SILSESQUIOXANES

(76) Inventors: Jason T. Flodin, 3284 W. Cedar St., Allentown, PA (US) 18104; Joseph D. Lichtenhan, 2 Chestnut Point, Petal, MS (US) 39465; Joseph J. Schwab, 16352 Bradbury La., Huntington Beach, CA (US) 92647; Yi-Zhong An, 12 Walnut Creek, Irvine, CA (US) 92602; Xuan Fu, 15 Timber Ridge, Purvis, MS (US) 39425; Zachary Kemp, 174 Jerry Kemp Rd., Mendenhall, MS (US) 39114

( * ) Notice: Subject to any disclaimer, the term of this patent is extended or adjusted under 35 U.S.C. 154(b) by 274 days.

(21) Appl. No.: 11/379,993

(22) Filed: Apr. 24, 2006

(65) Prior Publication Data

US 2009/0176006 A1    Jul. 9, 2009

Related U.S. Application Data

(60) Provisional application No. 60/673,880, filed on Apr. 22, 2005.

(51) Int. Cl.
*C08F 30/08* (2006.01)
(52) U.S. Cl. .................. 526/279; 526/321; 526/328; 526/347; 524/268
(58) Field of Classification Search ............. 526/279, 526/321, 328.5, 347; 524/268
See application file for complete search history.

(56) References Cited

U.S. PATENT DOCUMENTS

| 5,412,053 | A | 5/1995 | Lichtenhan et al. |
|---|---|---|---|
| 5,484,867 | A | 1/1996 | Lichtenhan et al. |
| 5,858,544 | A | 1/1999 | Banaszak Holl et al. |
| 6,069,295 | A | 5/2000 | Leitao |
| 6,444,318 | B1 | 9/2002 | Guire et al. |
| 6,586,548 | B2 * | 7/2003 | Bonafini et al. ............. 526/279 |
| 6,653,365 | B2 | 11/2003 | Jia |
| 2004/0054047 | A1 * | 3/2004 | Lai et al. ..................... 524/268 |
| 2004/0068075 | A1 | 4/2004 | Lichtenhan |
| 2004/0120915 | A1 | 6/2004 | Yang et al. |
| 2004/0202623 | A1 | 10/2004 | Quadir |

* cited by examiner

*Primary Examiner*—Elvis O Price
(74) *Attorney, Agent, or Firm*—David H. Jaffer; Pillsbury Winthrop Shaw PIttman LLP

(57) ABSTRACT

Nanostructured chemicals such as polyhedral oligomeric silsesquioxanes, polyhedral oligomeric silicates, and polyhedral oligomeric metallasesquioxanes are attached to living and nonliving systems as biomaterials to provide a nanoscopic topology that favors biomimetic function and cellular modulation. The resulting surface is nanoscopically thin, nanoscopically dispersed, provides systematic chemistry, surface area, surface volume, surface topology, and is essentially free of impurities, and has controllable properties through selection of composition, R groups, nanostructure size and topology. Highly shape specific and chemically tailorable nanostructured molecules are sized to biological material dimensions and are compatible with all sterilization methods.

7 Claims, 11 Drawing Sheets

CPTi 2 weeks after culture

CPTi + POSS 2 weeks after culture

The Upper 2 figures are immunohistochemistry of normal Ti cultured with bone stroma cells. The lower 2 figures are immunohistochemistry of Ti coated with Sample 2.

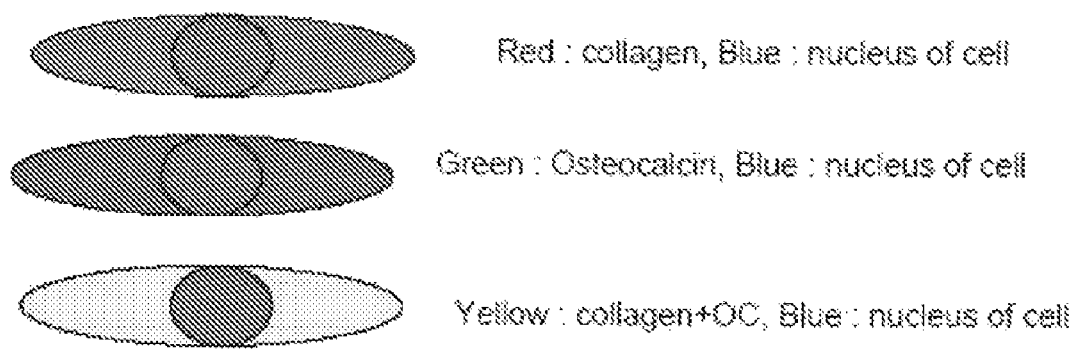

Red : collagen, Blue : nucleus of cell

Green : Osteocalcin, Blue : nucleus of cell

Yellow : collagen+OC, Blue : nucleus of cell

|  | Labeled cell | Collagen | OC | Co+OC |
|---|---|---|---|---|
| Control | 26% | 12% | 10% | 4% |
| S2 | 59% | 34% | 15% | 10% |

The OC is an extracellular matrix protein which produces by fully differntiated osteoblasts. This cell counting is not cover whole area of Disk, but this data suggests Osteoposs may stimulate differentiation of osteoblast.

FIG. 8

R = Trifluoropropyl

[(TrifluoropropylSiO1.5)12]Σ12

$C_{36}H_{48}F_{36}O_{18}Si_{12}$

FL0577

R = iOctyl

[(iOctylSiO1.5)8]Σ8

$C_{64}H_{136}O_{12}Si_8$

MS0805

R = iButyl

[(iButylSiO1.5)8]Σ8

$C_{32}H_{72}O_{12}Si_8$

MS0825

R = Phenyl

[(PhenylSiO1.5)8]Σ8

$C_{48}H_{40}O_{12}Si_8$

MS0840

R = Vinyl

[(VinylSiO1.5)8]Σ8

$C_{16}H_{24}O_{12}Si_8$

OL1160

R = Vinyl

[(VinylSiO1.5)10]Σ10

$C_{20}H_{30}O_{15}Si_{10}$

OL1170

R = Vinyl

[(VinylSiO1.5)n(Vinyl(OH)SiO1.0)m]

$(C_2H_3O_{1.5}Si)_x$

PM1283

R = Ethyl

[(EthylSiO1.5)4(Ethyl(OH)SiO1.0)3]Σ7

$C_{14}H_{36}O_{12}Si_7$

SO1444

R = iButyl

[(iButylSiO1.5)4(iButyl(OH)SiO1.0)3]Σ7

$C_{28}H_{66}O_{12}Si_7$

SO1450

R = iOctyl

[(isoOctylSiO1.5)4(isoOctyl(OH)SiO1.0)3]Σ7

$C_{56}H_{122}O_{12}Si_7$

SO1455

R = Phenyl

[(PhenylSiO1.5)4(Phenyl(OH)SiO1.0)3]Σ7

$C_{42}H_{38}O_{12}Si_7$

SO1458

BIOMIMETIC MATERIALS COMPRISING POLYHEDRAL OLIGOMERIC SILSESQUIOXANES

CROSS-REFERENCE TO RELATED APPLICATIONS

This application claims the benefit of U.S. Provisional Application Ser. No. 60/673,880 filed on Apr. 22, 2005.

BACKGROUND OF THE INVENTION

Biomaterials, as such Polyhedral Oligomeric Silsesquioxanes (POSS) and Polyhedral Oligomeric Silicates (POS), may be fabricated by the incorporation of POSS molecules into material for the purpose of providing a nanoscopic topology which favors cellular modulation, bioavailability, and differentiation.

POSS silanol biomaterials have been seen to initially coordinate to metal and ceramic implant surfaces through hydrogen bonding and further react via the elimination of either hydrogen gas or water to form a thermodynamically favored silicon-oxygen-metal bond The resulting surface is nanoscopically thin, and may be tailored to produce a uniform mono layer or a porous self assembled network providing a nanoscopic topology essentially free of impurities and controllable through selection of composition, R groups, nanostructure size and topology.

Highly rigid, shape specific, chemically tailorable nanostructures such as POSS molecules are desirable as they coordinate surface characteristics at the nanoscale, and provide a surface that is compatible with all sterilization methods. In vitro immunohistochemistry experiments have shown that certain types of POSS nanostructures cause the proliferation and differentiation of bone stroma cell (BSC) and the deposition of apatite. This proliferation and differentiation of BSC provides an indication that POSS nanostructures of appropriate form are bioactive, and therefore also biocompatible and resorbable. POSS biomaterials may also incorporate amino acid sequences, peptides, phosphates, apatites, carbonates, silicates, and related bioactive elements, chemicals, or reagents in combination with POSS cages functionalized with $R=R^1$ hydrocarbon and $R=R^2$ biologically active groups on the $[(RSiO_{1.5})_7(HOSiO_{1.5})_1]_{\Sigma 8}$, $[(RSiO_{1.5})_6(R(HO)SiO_1)_2]_{\Sigma 8}$, $[(RSiO_{1.5})_2(R(HO)SiO_1)_4]_{\Sigma 6}$. $[(RSiO_{1.5})_4(R(HO)SiO_1)_3]_{\Sigma 7}$ and larger sized cages and cage fragments of formula types such as $[(RSiO_{1.5})_2(R(HO)SiO_1)_4]_{\Sigma 6}$, $(RSi(HO)O)_4)$, $(RSi(OH)_2)_2O$.

FIELD OF THE INVENTION

The present invention relates to biomaterials that are enabled by the manipulation and development of POSS, POS, and POMS compounds from readily available and low-cost silicon containing feedstocks. Examples of these low cost feedstocks include but are not limited to: Polysilsesquioxanes $[RSiO_{1.5}]_{\Sigma 8}$, homoleptic Polyhedral Oligomeric Silsesquioxanes (POSS) $[(RSiO_{1.5})_n]_{\Sigma\#}$, functionalized homoleptic POSS $[(RSiO_{1.5})_m(RXSiO_{1.0})_n]_{\Sigma\#}$, heteroleptic POSS $[(RSiO_{1.5})_m(R'SiO_{1.5})_n]_{\Sigma\#}$, functionalized heteroleptic POSS $[(RSiO_{1.5})_m(R'SiO_{1.5})_n(RXSiO_{1.0})_p]_{\Sigma\#}$, polyhedral oligomeric silicates $[(XSiO_{1.5})_n]_{\Sigma\#}$, and POSS fragments $[(RXSiO_{1.5})_n]$.

As defined by the present invention a "biomaterial" is a material that is intended to interact with biological systems. Biomaterial-tissue interactions are best defined by the following terms: "biocompatibile", "bioinert", "bioactive", "biomimetic", "resorbable". Stringently defined, biocompatibility is the ability of a material to extract an appropriate biological response in a particular biological environment. This definition implies that any material placed on or into the body will not be inert and will interact with tissues in a dynamic way, altering both the material and the tissues around it. The biological response to a material is critically dependent on five factors: (i) the composition, (ii) surface structure, (iii) topology, (iv) biology of the host site, and (v) the physicomechanical demands on the material.

Biomaterial-tissue interactions are relevant to a wide variety of applications and treatments. Traditionally, the area of biomaterials has focused on materials which can support or replace lost human tissue, for example in orthopedics (femoral implants), vascular biology (arterial stents), and dentistry (filling materials/implants/material-tooth bonding). Currently biomaterials-tissue interactions have been involved in an area called tissue engineering or bioengineering. Roughly defined, tissue engineering is the manipulation of developmental or wound healing processes to repair or replace lost tissue. In this area, biomaterials have been used as permanent or resorbable scaffolds (for cells or other critical molecules), drug-delivery devices, and barrier materials. For example, cartilage cells may be seeded onto a resorbable scaffold, implanted, and allowed to support cartilage development. In many cases, biocompatibility is critical to the success of these treatment strategies. Recently biomaterials have also been used in more non-traditional applications such as imaging, cosmetics, and nutritional supplements. Esthetic applications include maxillofacial prostheses to restore facial contours after surgical treatment for cancer, or in dentistry to restore tooth esthetics after trauma or dental disease.

Nanostructured biomaterials are best exemplified by those based on low-cost Polyhedral Oligomeric Silsesquioxanes (POSS) and Polyhedral Oligomeric Silicates (POS and Polyhedral Oligomeric Metallasesquioxanes). POSS, POS, and POMS systems contain hybrid (i.e., organic-inorganic) compositions in which the hollow internal cage like framework is primarily comprised of inorganic silicon-oxygen bonds. The exterior of the nanostructure is covered by both reactive and nonreactive organic functionalities (R), which ensure compatibility and tailorability of the nanostructure with manmade and biological tissues. These and other properties and features of nanostructured chemicals are discussed in detail in U.S. Pat. No. 5,412,053 and U.S. Pat. No. 5,484,867 to Lichtenhan et al., both are expressly incorporated herein by reference in their entirety.

Significant opportunity exists for technology that can form compatible interfaces between man-made and biological systems. The need is especially acute for prosthetic implants. The U.S. market for total and partial joint replacement is an ever-growing market with over 500,000 procedures being preformed each year in a $2 billion industry. An important and growing component of this market is the use of bioactive compounds, and surface treatments. Materials such as metals, ceramics, and polymers have been used for decades in an effort to reduce foreign body reaction and increase integration with limited success.

Of key importance is the fundamental fact that the interaction between solid surfaces and biological systems are critically important to this field. In general, only the surface of an implanted material is in direct contact with the host tissue, and thus this portion of the material plays a critical role in long term fixation and biocompatibility.

Many prior efforts have been made to compatibilize the surface of implants with biological systems. These efforts have included numerous compounding, grafting, and coating methods employing polymeric, single—multiple layer and ceramic coatings (see U.S. Pat. Nos. 6,444,318 and 6,069, 295). The promise of polyhedral oligomeric silsesquioxane for biocompatible materials lies in their rigid shape, tailorable R group, highly dispersive nature, and hybrid inorganic-organic three-dimensional structure which provides a specific surface area and topology. The also have the ability to provide stereospecific delivery of reactive groups such as silanol (Si—OH) groups to promote attachment. The ability of polyhedral oligomeric silsesquioxanes to provide specific surface coverage (metals, glass, etc.) to substrates to nonbiological substrates has been shown in U.S. Pat. No. 5,858,544.

Moreover, the most promising property of nanostructured chemicals (POSS, POS, POMS) lies in their ability to rationally control surface area, volume, and roughness. This control in turn affords the ability to stimulate biological response at nanoscopic dimensions, such as the initiation and formation of cellular bonding and response such as apatite, the major inorganic component of bone. It has been seen that the inability of current implant formulations and coatings (such as titanium, titanium-based alloys, and inorganic bio-ceramics) to mimic the physicochemical, mechanical interface, and nanometer geometry found in bone results in inefficient and incomplete bonding, and crack propagation to juxtaposed bone (i.e. insufficient osseointegration and substrate failure). By controlling implant surface area and roughness with the present invention, osseointegration is promoted and provides mechanical stability to the implant in situ, minimizes motion-induced damage to surrounding tissues, and is imperative for the clinical success of bone implants.

Bonding of an orthopaedic implant to juxtaposed bone (i.e. osseointegration) is a critical characteristic that determines implant efficacy. Osseointegration is necessary to stabilize the prostheses in situ so that physiological loading conditions can be supported and, consequently, the patient can lead a normal, active life. Incomplete osseointegration of prostheses can be caused by surface properties that (i) do not promote cellular adhesion, (ii) do not support new bone growth, or (iii) have mechanical properties that do not match those of surrounding bone tissue. Mismatch of mechanical properties between an implant and surrounding bone can lead to stress and strain imbalances that cause implant loosening, failure, and eventual surgical removal.

Unfortunately, current material formulations utilized as bone prostheses (e.g. commercially pure titanium, Ti-6Al-4V, and Co—Cr—Mo alloys) do not simultaneously satisfy the surface and mechanical requirements necessary for increased implant efficacy. This is not surprising since, historically, these materials were developed for applications other than to serve as implants (such as for building constructs, aeronautical engineering, etc.). Such materials were chosen as long as they were tolerated by the human body and met certain physiological force requirements. Failure of these metals and metal alloys are often due to poor surface properties that result in insufficient bonding with juxtaposed bone. Ceramics have also been proposed to serve as orthopedic implant materials. However, ceramics, although possessing exceptional cytocompatibility properties with bone cells, have experienced little use as single-component orthopaedic implants due to poor mechanical properties (such as low fracture toughness) under physiological loading conditions. When loaded, poor mechanical properties of ceramics often lead to crack initiation and propagation events that necessitate surgical removal of failed implants. Even when used as a coating, ceramics often dissolve or fracture before promotion of new bone growth and, thus, often leave a base metal alloy material which was insufficient to support osseointegration in the first place.

As previously mentioned bio-ceramics such as, hydroxylapatite and calcium phosphate are quite brittle, and the failure of fixation between bone and the prosthesis may occur. The ideal thickness for these coatings is approximately 20-70 microns (plasma spray deposition). Newer low temperature deposition techniques have also been developed using organics, calcium, and phosphates, which is known to the art as surface-induced mineralization. These coatings have a reported thickness in the order of 5-10 µm. Although these advanced application methods produce uniform ceramic coatings in the micron to nanometer range they are nevertheless susceptible to interfacial failure and remain very brittle. Newer implant designs have been achieved to combat the physical weaknesses of these bio-ceramic coatings. These design features have been incorporated into high stress implants and allow the bio-ceramic coating to be loaded in compression rather than shear force. Such materials however shield by design pose as interfacial failure points. Either new material formulations which simultaneously possess sufficient surface and mechanical properties or novel techniques are required in order to initially form and maintain adequate bonding amid substrate and surrounding bone throughout a patient's life.

Furthermore, several concerns about current coating materials and techniques have been raised and are currently being studied. Noted concerns include bond failure between substrate and coating, leading to loosening of the component and ultimate failure of fixation. This substrate coating failure or wear may also lead to particulate debris which induce an immune inflammatory response cascading to osteolysis.

The need for a coating to mimic the physicochemical, mechanical interface, and nanometer geometry found in bone not subject to particulate debris is realized in the present invention. This novel combination of properties is achieved through the binding of three dimensional structurally rigid, 1.5 nm POSS nanostructured chemicals to the surface of prosthetics. Such control is desirable in that it affords rational control over surface design and function. Furthermore, it enhances surface tailorability toward improved biological fixation, and reliability, through the presence of well defined nanotopology. Compatabilization of macroscopic prosthetic surfaces at the nanoscopic level (one billionth of a meter features) with hybrid organic-inorganic nanoscopic cages is desirable as it allows for an increased surface area. An appropriate interfacial relationship provides mechanical stability to the implant in situ, minimizing motion-induced damage to surrounding tissues, and is imperative for the clinical success of bone implants, and the incorporation of the nanoagents into the know hierarchy of bone and tissue structures (Table 1).

Table 1 lists the size range of hollow POSS cages relative to cell dimensions and tissue structural features. The size of POSS is roughly equivalent to the overall dimensions of diameters for several biomaterials, thus at a nanoscopic level POSS can effectively mimic biological topology and thereby encourage cellular integration in tissue organization and structure.

TABLE 1

Relative sizes of POSS, cell types, and tissue structural features

| Biomaterial | Diameter |
|---|---|
| Osteoblast Cells | 10000 nm |
| Liver Cells | 4000-8000 nm |
| Red Blood Cells | 760 nm |
| Collagen Helices | 1.5 nm |
| Blood Capillary Pore | 4-8 nm |
| Wood Cell Wall | 2.5 nm |
| Hydroxyapatite Crystallites | 5 nm |
| Octacyclohexyl POSS | 1.5 nm |

This invention describes the use of POSS nanostructured hybrid "organic-inorganic" chemicals as biomaterials. Prior art with nanostructured polyhedral oligomeric silsesquioxanes (POSS and POS and POMS), has reported their utility as corrosion resistant materials (U.S. Pat. No. 5,858,544) utility for the control of grain structure and aging characteristics of metallic solder alloys, and use of POSS in personal care and medical material applications (U.S. Publication No. 2004/0120915; U.S. Pat. Nos. 6,586,548 and 6,653,365). This prior art makes no mention of their application and utility as biomaterials or as interfacial biomimetic constructs to improve cell modulation or physical properties.

Nanostructured chemicals and in particular POSS cages are the preferred species for modification of implants (FIG. 1). Furthermore, the dispersion of the POSS molecules and their compatibility with implant materials and surrounding tissue is thermodynamically governed by the free energy of mixing equation ($\Delta G=\Delta H-T\Delta S$). The nature of the R group and ability of the reactive groups on the POSS cage to react or interact with polymers and surfaces greatly contributes to a favorable enthalpic ($\Delta H$) term while the entropic term ($\Delta S$) for POSS is highly favorable when the cage size is monoscopic and the corresponding distribution of oligomers is 1.0.

SUMMARY OF THE INVENTION

The present invention provides a biomaterial comprising of a nanostructured chemical preferably from the group of POSS, POS, POMS of the type and combinations thereof with other nanostructured chemicals, nanoparticles or materials of natural or biological origin. Nanostructured chemicals are preferred for use as biomaterials as they are highly dispersible, have systematically controlled chemistry, surface area, surface volume, topology and selectivity in promoting cellular modulation and properties.

A simple example of such a biomaterial is the reaction of a POSS silanol $[(R^1SiO_{1.5})_4(R^1HOSiO_1)_3]_{\Sigma 7}$ (where $R^1$=Ph) to coat a titanium implant and consequently promote the binding and cellular modulation leading to bone formation. A second simple example is the reaction of the formula $[(R^1SiO_{1.5})_4(R^1HOSiO_1)_3]_{\Sigma 7}$ (where $R^1$=isooctyl) with soft tissue to promote binding and cellular modulation leading to formation of soft tissue.

BRIEF DESCRIPTION OF THE DRAWINGS

FIG. 8 illustrates the immunohistochemistry of Ti cultured with bone stroma cells.

DETAILED DESCRIPTION

Definition of Formula Representations for Nanostructures

Figure 1:
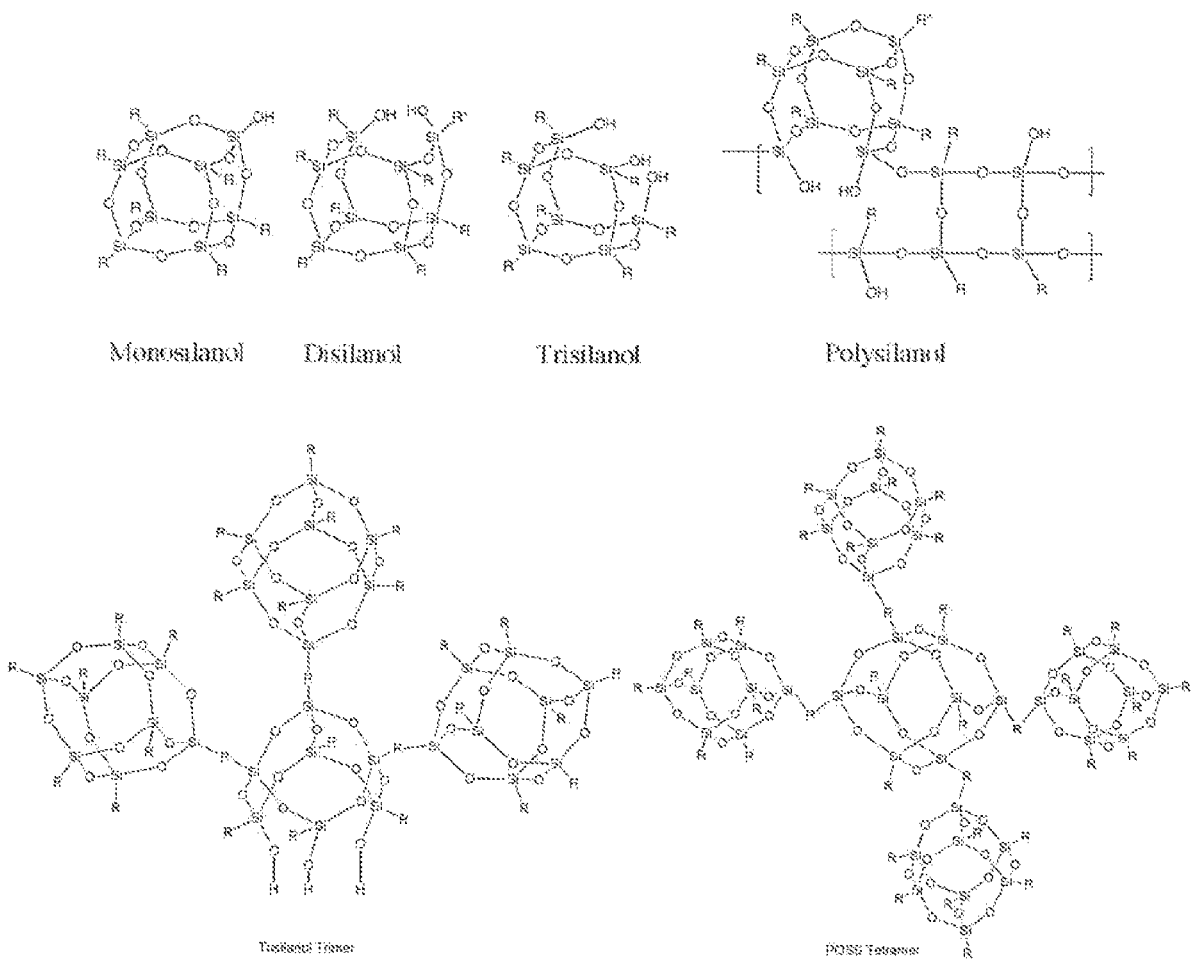
FIG. 1 shows a comparison of hollow and structurally rigid POSS nanostructured chemicals.
Figure 2:
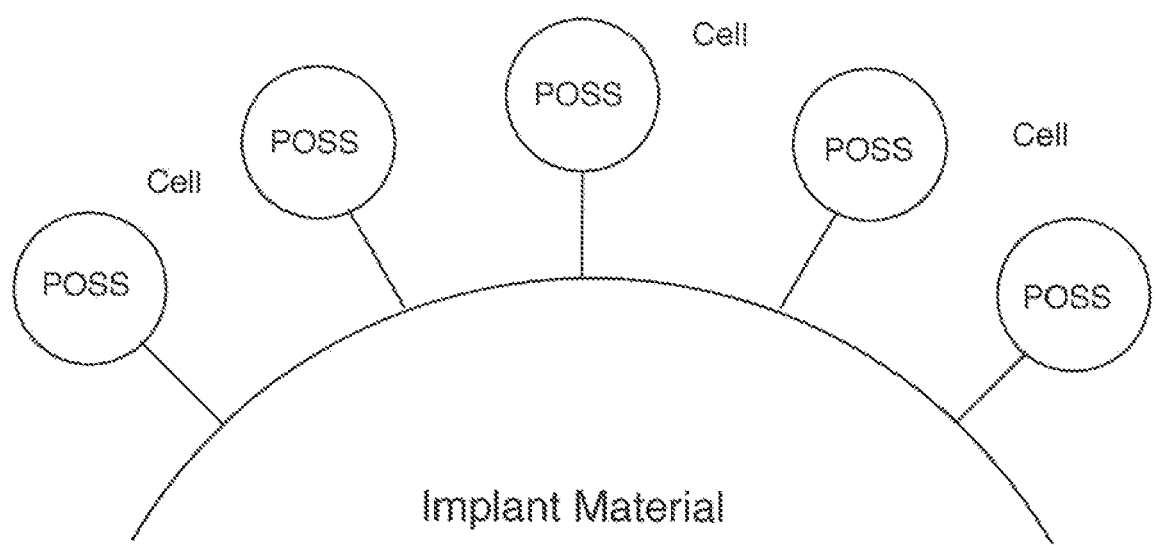
FIG. 2 illustrates multi-length scale reinforcement (nano-macro) provided through POSS-surface modification of nanoscopic and macroscopic surfaces.
Figure 3A:
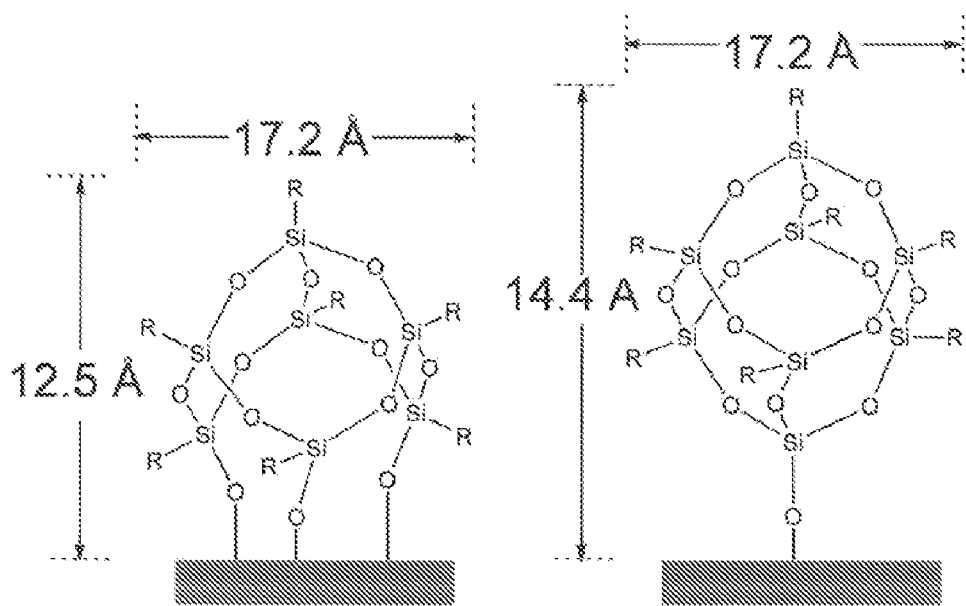
FIGS. 3A, 3B and 3C illustrate surface area and topological control at the nanoscopic level from nanostructured chemicals as monolayer coatings.
Figure 3B:
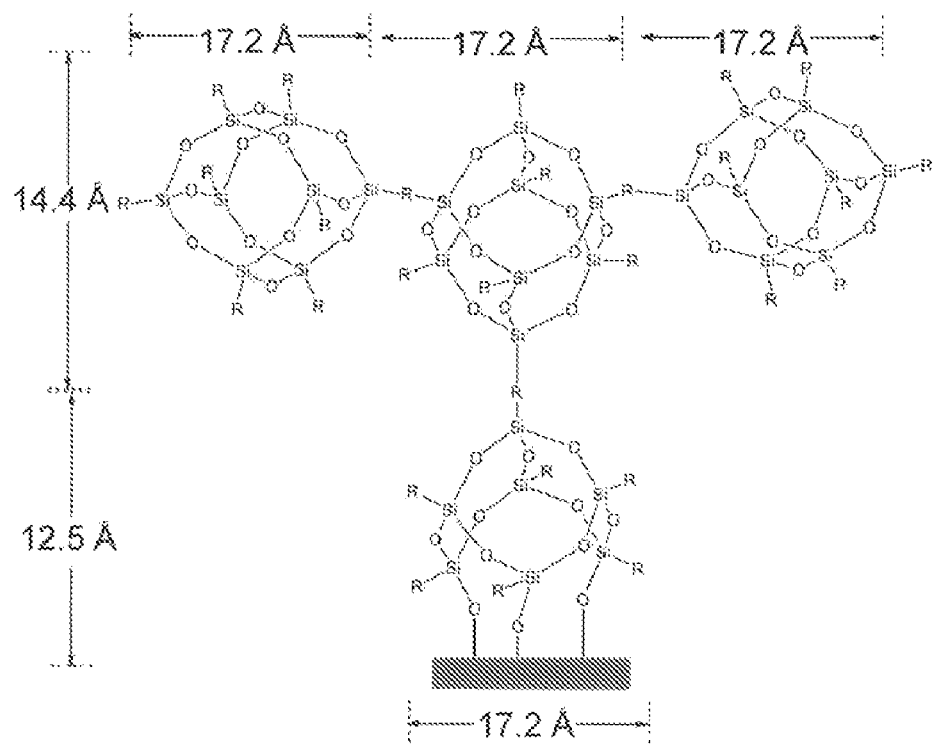
Figure 3C:
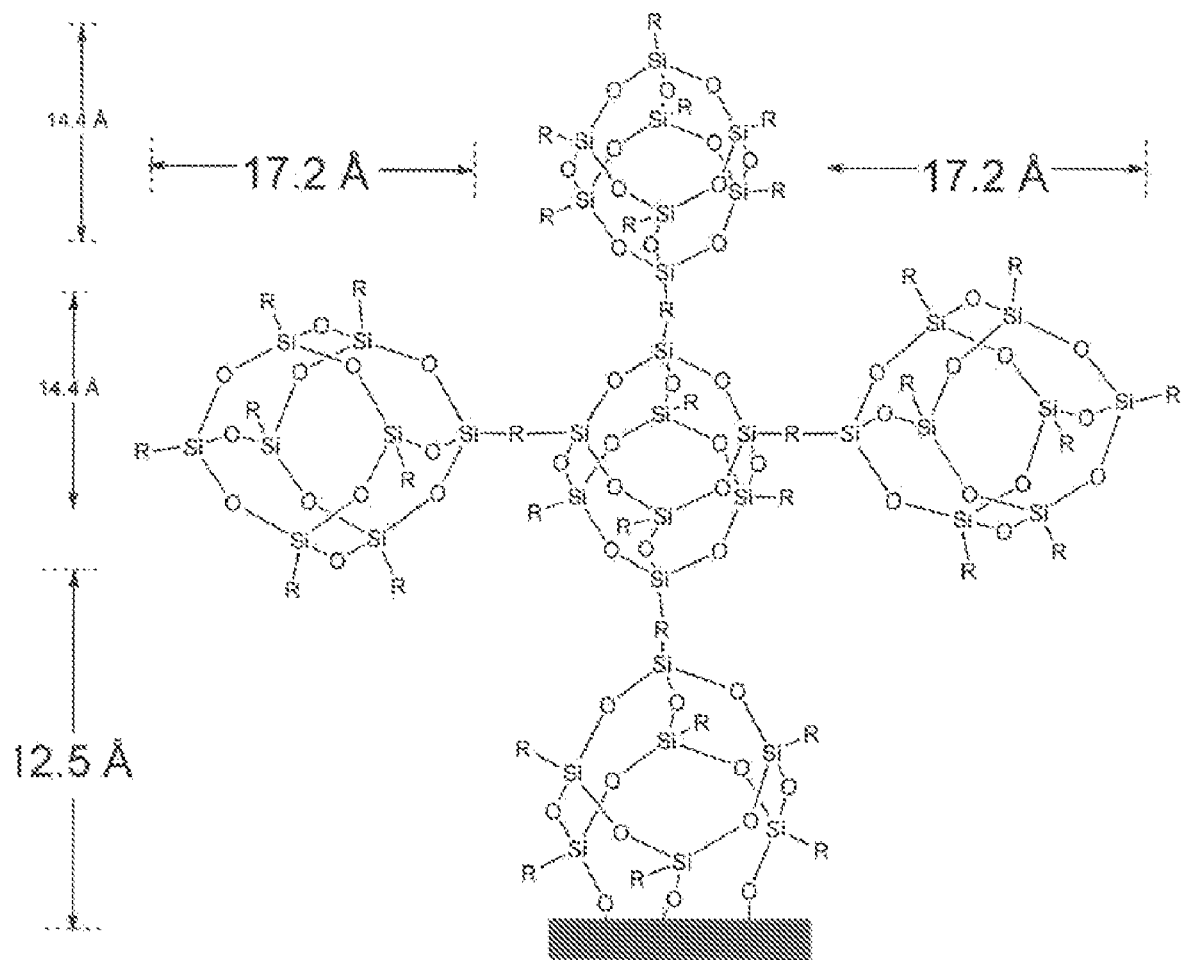
Figure 4:
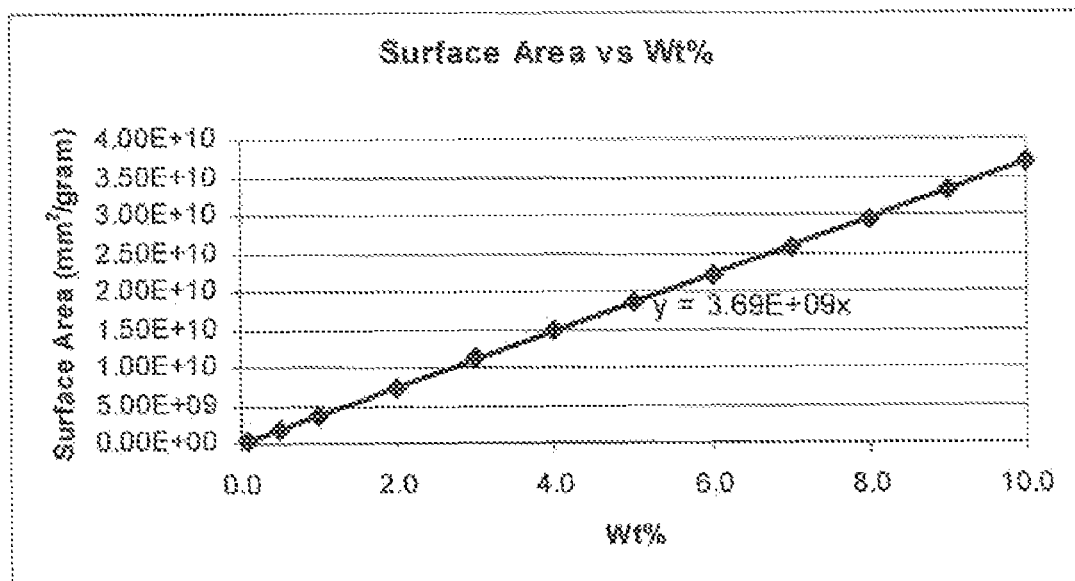
FIG. 4 shows volume contribution relative to weight percentage loading from adding a 1 nm nanostructured chemical.
Figure 5:
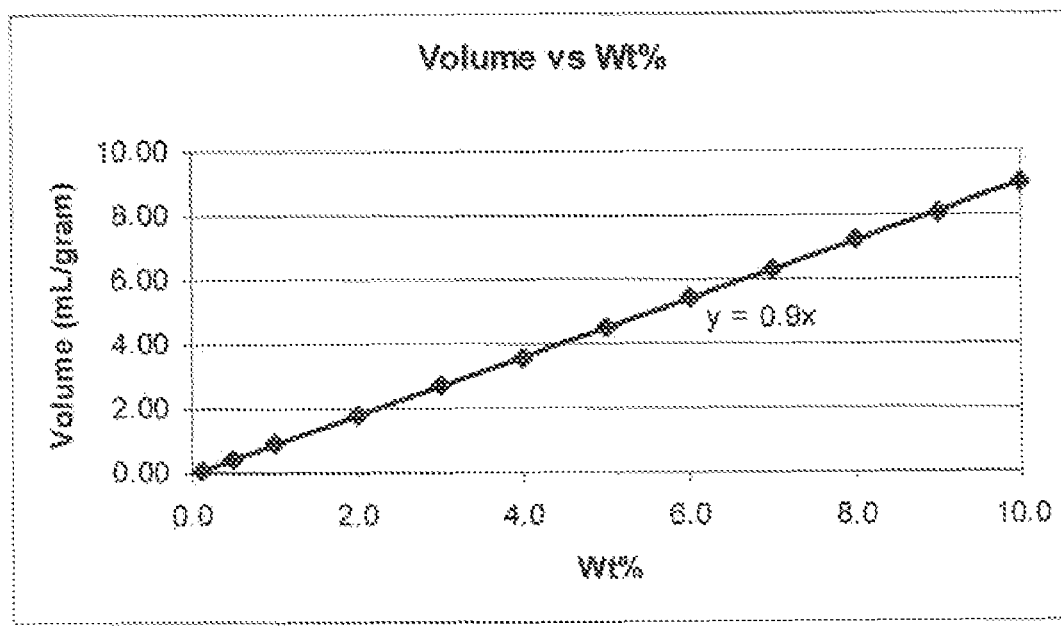
FIG. 5 illustrates surface area contribution relative to weight percentage loading from adding a 1 nm nanostructured chemical.

For the purposes of understanding this invention's chemical compositions, the following definitions are made for formula representations of Polyhedral Oligomeric Silsesquioxane (POSS) and Polyhedral Oligomeric Silicate (POS) nanostructures.

Polysilsesquioxanes are materials represented by the formula $[RSiO_{1.5}]_\infty$, where $\infty$ represents molar degree of polymerization and R=represents an organic substituent (H, siloxy, cyclic or linear aliphatic or aromatic groups that may additionally contain reactive functionalities such as alcohols, esters, amines, ketones, olefins, ethers or halides or which may contain fluorinated groups). Polysilsesquioxanes may be either homoleptic or heteroleptic. Homoleptic systems contain only one type of R group while heteroleptic systems contain more than one type of R group.

POSS and POS nanostructure compositions are represented by the formula:

$[(RSiO_{1.5})_n]_{\Sigma \#}$ for homoleptic compositions $[(RSiO_{1.5})_n(R'SiO_{1.5})_m]_{\Sigma \#}$ for heteroleptic compositions (where R≠R')

$[(RSiO_{1.5})_n(RXSiO_{1.0})_m]_{\Sigma \#}$ for functionalized heteroleptic compositions (where R groups can be equivalent or in equivalent)

$[(RSiO_{1.5})_n(RSiO_{1.0})_m(M)_j]_{\Sigma \#}$ for heterofunctionalized heteroleptic compositions In all of the above R is the same as defined above and X includes but is not limited to OH, Cl, Br, I, alkoxide (OR), formate (OCH), acetate (OCOR), acid (OCOH), ester (OCOR), peroxide (OOR), amine ($NR_2$), isocyanate (NCO), sugars, peptides, and biological groups. The symbol M refers to metallic elements within the composition that include high and low Z metals including s and p block metals, d and f block transition, lanthanide, and actinide metals. In particular, the metals Al, B, Ga, Gd, Ce, W, Ni, Eu, Y, Zn, Mn, Os, Ir, Ta, Cd, Cu, Ag, V, As, Tb, In, Ba, Ti, Sm, Sr, Pb, Lu, Cs, Tl, Te are useful. The symbols m and n refer to the stoichiometry of the composition. The symbol $\Sigma$ indicates that the composition forms a nanostructure and the symbol # refers to the number of silicon atoms contained within the nanostructure. The value for # is usually the sum of m+n, where n ranges typically from 1 to 24 and m ranges typically from 1 to 12. It should be noted that $\Sigma\#$ is not to be confused as a multiplier for determining stoichiometry, as it merely describes the overall nanostructural characteristics of the system (aka cage size).

The present invention teaches an improved method of designing the surface topology of biomaterials via the use of hollow and structurally rigid POSS nanostructured chemicals as nanoscopic biomaterials and biomimetic surface modifers.

A key feature of the present invention is the use of the three dimensional rigid POSS cage structures to induce proliferation and differentiation of osteoblastic and fibroblastic cells to the surface of implants. The assembly of POSS cages on or within a substrate surface provides a means to promote select cellular adhesion to the prosthesis and biological fixation of the POSS structure into juxtaposed bone. A range of cage sizes and formula are applicable and include POSS cages containing one or more R groups such as mono through tetra peptides (e.g. RGD, KRSR) which are known to induce bone growth, and R groups such as glycocides and sugars (e.g. triterpene glycocides such as 27-deoxyactein) that are known to promote enzyme activity, and groups such as anti-inflammatory agents (e.g. heparin) and antibacterials (e.g. Ag+ cations, linezolid). The composition is not limited to these specific examples but can also contain additional biological factors. Biological factors include, for example, ascorbic acid-2-phosphate, dexamethasone, beta-glycerophosphate and TGF superfamily proteins, such as the bone morphogenic proteins (BMPs). The composition can also contain antibiotic, antimycotic, antiinflammatory, immunosuppressive and other types of therapeutic agents. There is tremendous value in the incorporation of POSS cages bearing mixtures of R groups present on the surface of an implant as it can serve to reduce infection and increase the rate of healing. The useful range of POSS silanol is from 0.01% to 99% on the surface of the implant with a preferred useful range of 0.1% to 10%.

The incorporation of POSS provides control over surface area, surface roughness, surface topology, and surface energy.

General Process Variables Applicable to all Processes

As is typical with chemical processes, there are a number of variables that can be used to control the purity, selectivity, rate and mechanism of any process. Variables influencing the process include the size and polydispersity, and composition of the nanostructured chemical, separation and isolation methods, and use of catalyst or cocatalysts, solvents and cosolvents. Additionally, kinetic and thermodynamic means of controlling the adhesion mechanism, rate, and product distribution are also known tools of the trade that can impact product performance, quality and economics.

EXAMPLE 1

Coating of $[(RSiO_{1.5})_4(R(HO)SiO_{1.0})_3]_{\Sigma 7}$ $[(RSiO_{1.5})_4(Rl(OH)SiO_{1.0})_3]_{\Sigma 7}$ (1 g) was dissolved in dichlormethane and sprayed onto metallic titanium samples. The samples were then dried at 110° C. for 2 hours.

Cell Adhesion Findings

Experimental samples with 50% surface coverage of POSS were exposed to osteoblasts and fibroblasts cultured in Dulbecco's modified eagle medium (DMEM), supplemented with 10% fetal bovine serum (FBS) and 1% penicillin streptomycin (P/S), under standard cell culture conditions (sterile chamber maintained at 37° C. and a humidified environment: 5% $CO_2$/95% air). The stock solutions were supplied by HyClone.

For this purpose, osteoblasts, and fibroblasts were separately seeded (10,000 cells $cm^2$) onto the experimental titanium substrate, and were allowed to adhere in standard cell culture conditions for 48 hours. After the prescribed time period, substrates were rinsed three times using phosphate-buffered saline (PBS) to remove non-adherent cells. The adhered cells were fixed with formaldehyde (Fisher), stained with Hoechst 33 258 dye (Sigma), and counted using fluorescence microscopy (365 nm excitation and 400 nm emission wavelengths). The findings in Table 2 indicate a clear differentiation in binding a cellular modulation relative to the type of R group present on the cage. Specifically, osteoblast exhibited a preference for $[(phenylSiO_{1.5})_4(phenyl(OH)SiO_{1.0})_3]_{\Sigma 7}$ while fibroplasts preferred $[(isoOctylSiO_{1.5})_4(isoOctyl(OH)SiO_{1.0})_3]_{\Sigma 7}$.

TABLE 2

Cellular adhesion measured in cell density/$cm^2$

| Sample | Osteoblast Cell Count | Fibroblast Cell Count |
|---|---|---|
| wrought titanium control | ~1,600/cm-2 | ~2,500/$cm^2$ |
| wrought titanium + $[(phenylSiO_{1.5})_4(phenyl(OH)SiO_{1.0})_3]_{\Sigma 7}$ | ~7,800/cm-2 | ~3,200/$cm^2$ |
| wrought titanium + $[(isoOctylSiO_{1.5})_4(isoOctyl(OH)SiO_{1.0})_3]_{\Sigma 7}$ | ~3,400/cm-2 | ~6,800/$cm^2$ |

All experiments were run in triplicate, and repeated three different times.

EXAMPLE 2

OsteoPOSS

Figure 6:
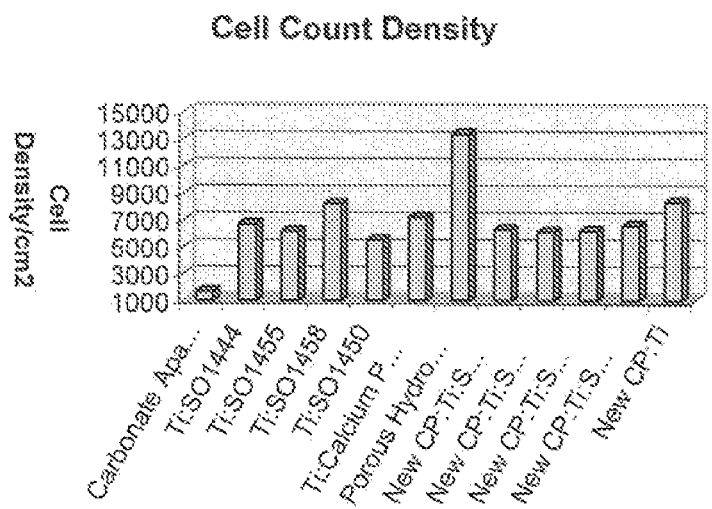
FIGS. 6 and 7 illustrate the use of $[(phenylSiO_{1.5})_4(phenyl(OH)SiO_{1.0})_3]_{\Sigma 7}$ to form bone in vitro.
Figure 7:
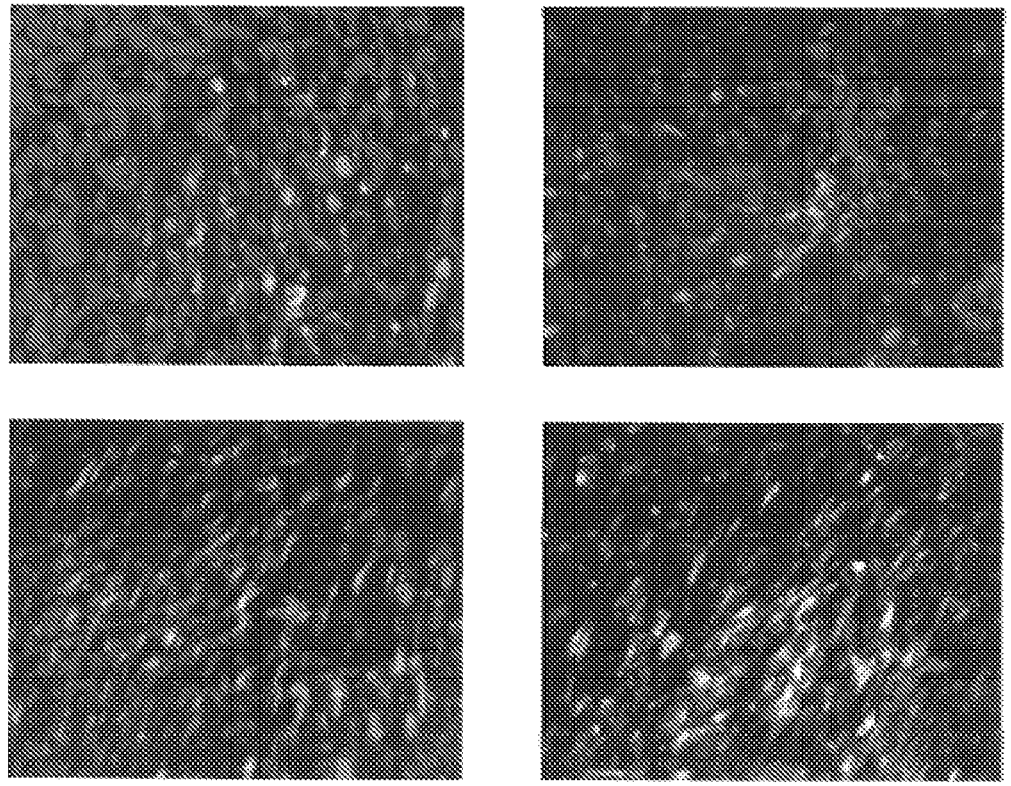

FIG. 6 illustrates the use of $[(phenylSiO_{1.5})_4(phenyl(OH)SiO_{1.0})_3]_{\Sigma 7}$ to form bone in vitro, eight POSS-bone samples 5 mm in length were implanted in vivo into rat calvaria as a bone defect. After one month the bone implantation site was examined and was found to be indistinguishable from normal rat bone. See FIGS. 7 and 8.

EXAMPLE 3

FibroPOSS

Based upon the differentiation from Example 1, a series of in vivo FibroPOSS examinations was made using $[(isoOctylSiO_{1.5})_4(isoOctyl(OH)SiO_{1.0})_3]_{\Sigma 7}$ and $[(isoOctylSiO_{0.5})_8]_{\Sigma 8}$. In a human arm a series of six cuts were made through the endermal skin layer.

The top two cuts were treated with 100% $[(isoOctylSiO_{1.5})_4(isoOctyl(OH)SiO_{1.0})_3]_{\Sigma 7}$(SO1455) and $[(isoOctylSiO_{1.5})_8]_{\Sigma 8}$ (MS0805).

The middle two cuts had 50/50 SO1450+bactin antibiotic and 50/50 MS0805+bactin antibiotic.

The bottom left cuts had 100% bactin antibiotic and the bottom right cut had no treatment.

All of the cuts healed at the same rate.

The two cuts treated with $[(isoOctylSiO_{1.5})_4(isoOctyl(OH)SiO_{1.0})_3]_{\Sigma 7}$ (SO1455) and $[(isoOctylSiO_{1.5})_8]_{\Sigma 8}$ (MS0805) did not show any bleeding after the POSS was added nor was visible clotting observed. The bottom two cuts did show bleeding and clotting was evident by scab formation. The $[(isoOctylSiO_{1.5})_4(isoOctyl(OH)SiO_{1.0})_3]_{\Sigma 7}$ SO1455) and $[(isoOctylSiO_{1.5})_8]_{\Sigma 8}$ (MS0805) are attributed to having stopped bleeding by plugging the 4-8 nm porosity between the endothelial capillary cells which in turn caused a hydrophobic constriction of the capillary and consequent stoppage of bleeding without clotting.

Figure 9A:
FIGS. 9A and 9B illustrate the formation of scar tissue treated with nanostructured chemicals.
Figure 9B:
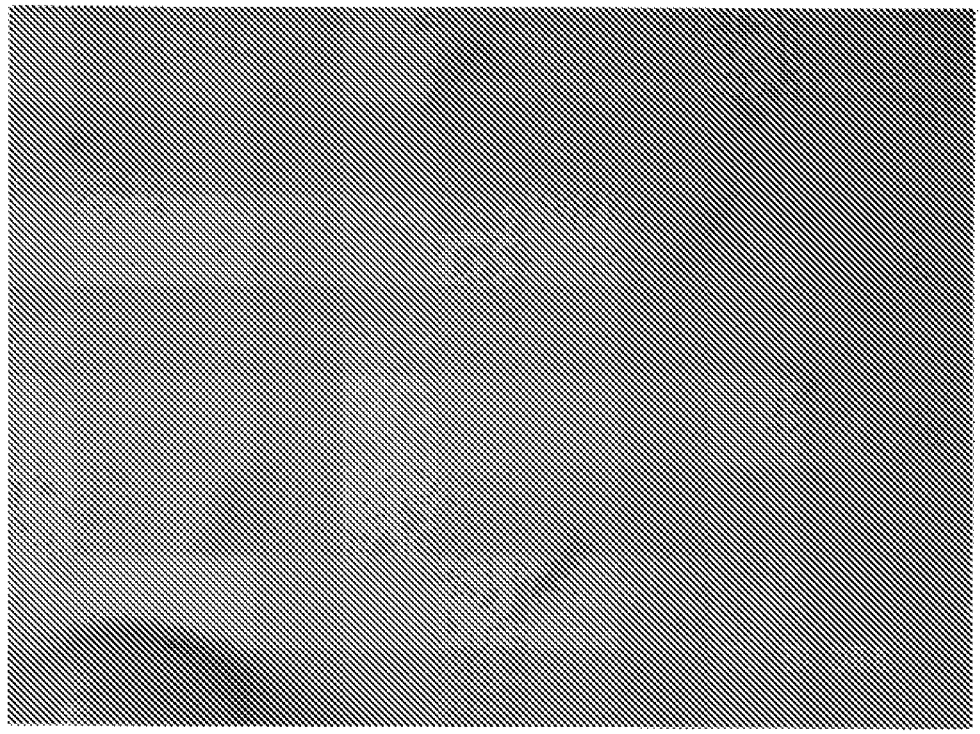
Figure 10A:
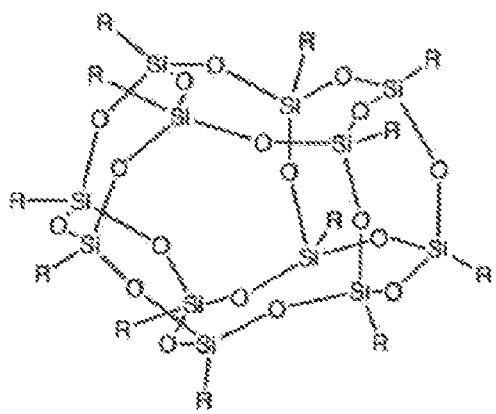
FIGS. 10A-10K provide examples of nanostructured chemicals suitable for incorporation into biomaterials.
Figure 10B:
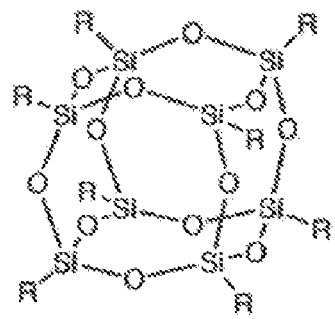
Figure 10C:
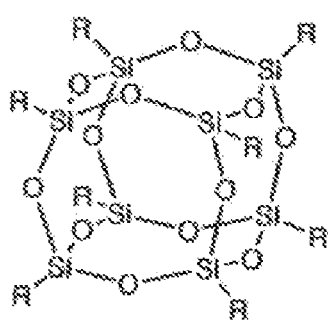
Figure 10D:
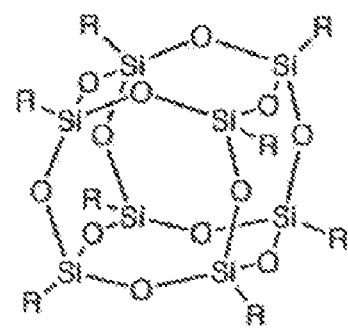
Figure 10E:
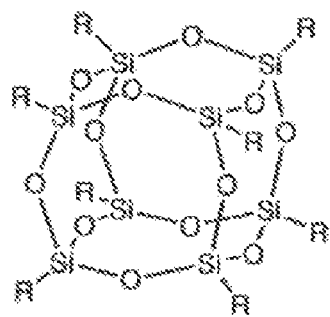
Figure 10F:
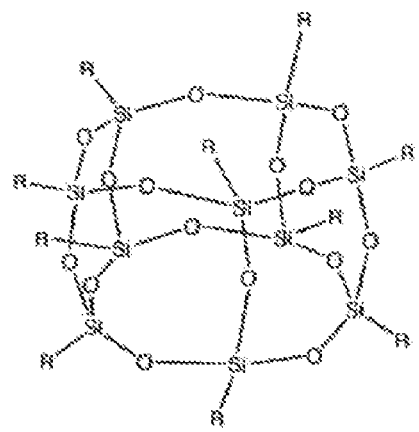
Figure 10G:
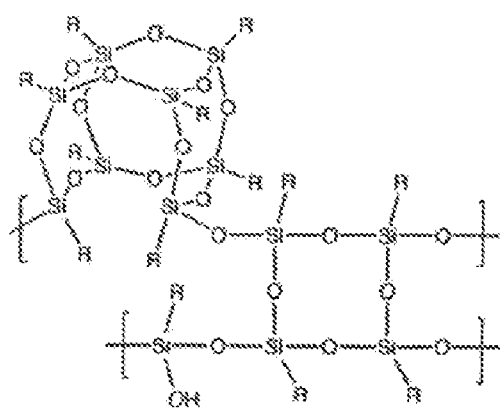
Figure 10H:
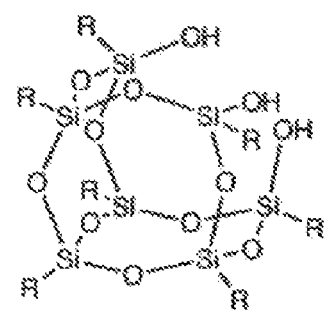
Figure 10I:
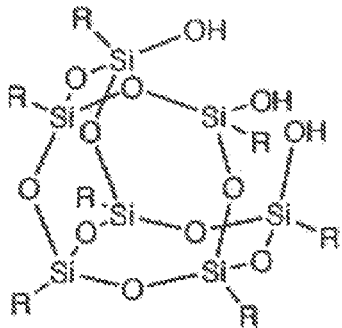
Figure 10J:
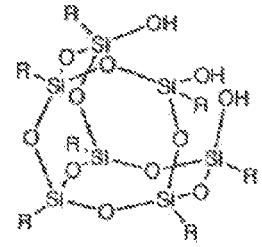
Figure 10K:
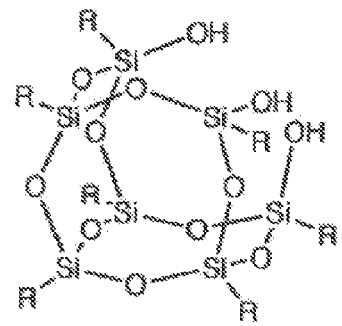

All of the cuts treated with the POSS formed oriented scar tissue. The formation of oriented scar tissue is evidence of enhanced fibroblast bonding and orientation these cells. See FIG. 9.

EXAMPLE 4

Application to Personal Care and Cosmetics

In light of the observed cellular differentiation and modulation promoted by nanostructured chemicals, a series of POSS, POS and POMS were added to conventional personal care and cosmetic products. This work was done to demonstrate the ability to add nanostructured chemicals to such products to promote biomimetic activity in such products without altertering their desirable product features, manufacturing methods, or method of application. A summary of the products and finding is listed below. Structure examples are shown in FIGS. 10A-10K.

Each sample prepared consisted of approximately 5% of POSS by weight and was inspected visually and by biometric techniques for the dispersion of the POSS compound. The products in which the POSS compounds could be dispersed without being felt are listed under the POSS compounds studied.

SO1450

Suave Shampoo, Right Guard Deodorant, Isoplus Styling Gel, Softsoap Bodywash, Clean & Clear Facewash, Nair Hair Remover, Nicel Face Cream, LA Colors Makeup, Hard as Nails Nail Polish, Smackers Lip Gloss.

SO1458

Dial Antibacterial Hand Soap, Suave Shampoo, Aveeno Lotion, Aquaphor Moisturizer, Right Guard Deodorant, Isoplus Styling Gel, Softsoap Bodywash, Clean & Clear Facewash, Nair Hair Remover, Nicel Face Cream, LA Colors Makeup, Hard as Nails Nail Polish (remained clear), Smackers Lip Gloss.

MS0840

Dial Antibacterial Hand Soap, Ivory Hand Soap, Suave Shampoo, Aveeno Lotion, Aquaphor Moisturizer, Right Guard Deodorant, Softsoap Bodywash, Clean & Clear Facewash, Nair Hair Remover, LA Colors Makeup, Hard as Nails Nail Polish, Smackers Lip Gloss.

OL1160

Dial Antibacterial Hand Soap, Ivory Hand Soap, Suave Shampoo, Aveeno Lotion, Aquaphor Moisturizer, Right Guard Deodorant, Softsoap Bodywash, Clean & Clear Facewash, Nair Hair Remover.

OL1170

Nicel Face Cream, LA Colors Makeup, Hard as Nails Nail Polish (remained clear) Smackers Lip Gloss (remained clear).

MS0825

Dial Antibacterial Hand Soap, Ivory Hand Soap, Suave Shampoo, Aveeno Lotion, Aquaphor Moisturizer, Right Guard Deodorant, Softsoap Bodywash, Clean & Clear Facewash, Nair Hair Remover, Nicel Face Cream, LA Colors Makeup, Hard as Nails Nail Polish (remained clear), Smackers Lip Gloss (remained clear).

MS0802

Dial Antibacterial Hand Soap, Ivory Hand Soap, Suave Shampoo, Aveeno Lotion, Aquaphor Moisturizer, Right Guard Deodorant, Softsoap Bodywash, Clean & Clear Facewash, Nair Hair Remover, Nicel Face Cream, LA Colors Makeup.

SO1455

Dial Antibacterial Hand Soap (remained clear), Ivory Hand Soap (remained clear), Suave Shampoo (remained clear), Aveeno Lotion, Aquaphor Moisturizer, Right Guard Deodorant (became thicker), Isoplus Styling Gel (became thicker), Softsoap Bodywash, Clean & Clear Facewash, Nair Hair Remover, Dollar General Astringent, 409 Cleaner, Glass Plus Cleaner Nicel Face Cream, Smackers Lip Gloss.

PM1285

Dial Antibacterial Hand Soap (remained clear), Ivory Hand Soap (remained clear), Suave Shampoo (remained clear) Aveeno Lotion, Aquaphor Moisturizer, Right Guard Deodorant, Isoplus Styling, Nair Hair Remover, Nicel Face Cream, Smackers Lip Gloss, Hard as Nails Nail Polish (became thicker).

While certain representative embodiments and details have been shown for purposes of illustrating the invention, it will be apparent to those skilled in the art that various changes in the methods and compositions disclosed herein may be made without departing from the scope of the invention which is defined in the claims.

What is claimed is:

1. A method of adapting a metal implant for osseointegration comprising coating a surface of the implant with a biomaterial including a compound selected from the group consisting of polyhedral oligomeric silsesquioxanes, polyhedral oligomeric silicates, and polyhedral oligomeric metallasesquioxanes, wherein a silanol functional group on the compound chemically bonds to the metal implant.

2. The method of claim 1, wherein the compound modifies the hydrophilicity or hydrophobicity of the biomaterial.

3. The method of claim 1, wherein the compound has a property selected from the group consisting of anti-inflammatory, cell-growth promoter, and antibacterial.

4. The method of claim 1, wherein the compound has a plurality of different organic substituent groups.

5. The method of claim 1, wherein a plurality of compounds having different organic substituent groups is used.

6. The method of claim 1, wherein a plurality of compounds having different cage sizes is used.

7. The method of claim 1, wherein the biomaterial is formed by a process selected from the group consisting of melt mixing with polymers, copolymerization, reactive chemical grafting, non-reactive grafting, vapor deposition, and sputtering.

* * * * *